United States Patent [19]

Sawicki

[11] Patent Number: 4,474,704

[45] Date of Patent: Oct. 2, 1984

[54] NOVEL PROCESS

[75] Inventor: Robert A. Sawicki, Wappingers Falls, N.Y.

[73] Assignee: Texaco Inc., White Plains, N.Y.

[21] Appl. No.: 267,211

[22] Filed: May 26, 1981

[51] Int. Cl.$^3$ ................................................ C07F 7/22
[52] U.S. Cl. ................................ 260/429.7; 260/429.5; 260/448 AD; 556/400; 556/446
[58] Field of Search .......... 260/448 AD, 429.7, 429.5; 556/400, 446

[56] References Cited

U.S. PATENT DOCUMENTS

| 3,242,201 | 3/1966 | Cramer et al. | 260/429.7 X |
| 3,308,149 | 3/1967 | Schenk | 556/446 |
| 3,488,370 | 1/1970 | Leary et al. | 260/448 AD |
| 3,541,126 | 11/1970 | Baronnier et al. | 260/429.7 X |
| 3,679,723 | 7/1972 | Tomomatsu | 260/448 AD |
| 4,083,860 | 4/1978 | Ruf | 260/448 AD |
| 4,164,509 | 8/1979 | Laüfer | 556/400 |

Primary Examiner—Helen M. S. Sneed
Attorney, Agent, or Firm—Robert A. Kulason; Carl G. Ries; Carl G. Seutter

[57] ABSTRACT

A novel catalyst, possessing phase transfer properties contains an alumina or silica substrate bearing poly(oxyethylene) or poly(oxypropylene) moieties bonded through a silicon atom to the substrate.

24 Claims, No Drawings

NOVEL PROCESS

FIELD OF THE INVENTION

This invention relates to a catalyst possessing phase transfer properties. More particularly it relates, in a specific embodiment, to a novel catalyst containing a poly(oxyethylene) or poly(oxypropylene) moiety bonded, through a silicon atom to a metal oxide substrate.

BACKGROUND OF THE INVENTION

As is well known to those skilled in the art, reactions between ionic reagents and non-polar reagents may be less than satisfactory because of the mutual immiscibility which generally characterizes the components of the system. Polar solvents such as dimethylformamide (DMF) or dimethyl sulfoxide (DMSO) may be employed; but use of such solvents introduces undesired problems. Glycols such as polyethylene glycol or polypropylene glycol may be used as solvents for such reactions; and indeed they possess many properties which render them satisfactory: low cost, low vapor pressure, low toxicity, and ready availability. However the difficulty of separating reaction product from eg polyethylene glycol is prohibitive because it requires extensive work-up such as distillation and/or extraction. See E. Santaniello et al *Tetrahedron Lett.*, 4581 (1979).

U.S. Pat. No. 4,173,693 to Dow as assignee of Au et al discloses products typified by the reaction product of a poly(ethylene glycol ether) and a chloromethylated polystyrene resin. U.S. Pat. No. 3,980,583 to Mobil as assignee of Mitchell et al discloses metal oxides bearing silicon coordinated typically to a Group VIII metal, through amine functionality. Tundo et al JACS 101:22 6605 (1979) discloses metal oxides bearing silicon plus amine functionality.

It is desirable to carry out reactions between ionic reagents and non-polar reagents using a phase transfer catalyst which is characterized by its ability to bring one of the reactants into the normal phase of the other in such a form that high reaction rates are obtained.

It is an object of this invention to provide a novel composition particularly characterized by its ability to serve as a phase transfer catalyst. Other objects will be apparent to those skilled in the art.

STATEMENT OF THE INVENTION

In accordance with certain of its aspects, this invention is directed to a process for preparing a functionalized porous refractory oxide which comprises (i) reacting a porous refractory oxide, bearing surface hydroxyl groups, with an organometal compound

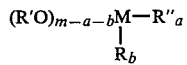

wherein R' is a lower alkyl hydrocarbon group having 1-8 carbon atoms, R is a lower alkyl hydrocarbon group having 1-8 carbon atoms, R" is a poly(oxyethylene) or poly(oxypropylene) residue having the formula

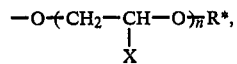

R* is hydrogen or a lower alkyl hydrocarbon group containing 1-8 carbon atoms, X is hydrogen or methyl, n is 1-300, M is an atom having a valence m greater than 1 selected from the group consisting of silicon, phosphorus, aluminum, titanium, tin, and boron, a is a positive integer less than m, and b is 0 or an integer less than m−1, thereby splitting out alcohol R'OH and forming functionalized oxide bearing at least one —O—M—R" group on the surface of said oxide; and (ii) recovering said functionalized oxide bearing at least one —O—M—R" group on the surface thereof.

DESCRIPTION OF THE INVENTION

The charge solid oxides which may be used as substrates in practice of the process of this invention may include a wide variety of porous refractory oxides typified by those which may commonly be used as inert catalyst supports. Although they may be used in impure form or as mixtures, more consistent results may be attained by the use of one species of pure porous refractory metal oxide. Illustrative of the porous refractory solid metal (including metalloid) oxides may be oxides of boron, magnesium, aluminum, silicon, phosphorus, calcium, titanium, vanadium, chromium, manganese, iron, cobalt, nickel, copper, zinc, arsenic, cadmium, barium, etc. It will be apparent that certain oxides typified by those of sodium may be too active under reaction conditions and may not be employed. Others may be too expensive. The preferred solid refractory oxides are those commonly referred to as inert and which have heretofore been proposed for use as catalyst supports. Most preferred are aluminum oxide ($Al_2O_3$) and silicon dioxide ($SiO_2$). Complex oxides may be employed viz: silica-magnesia; etc. It will be apparent that silicon is frequently referred to as a metalloid; but it is intended to be embraced within the term "metal" as used herein; and in fact silicon dioxide is a preferred charge solid porous refractory metal oxide. A preferred form of silica is that referred to as silica gel.

It is also possible to use as substrates refractory oxides which are crystalline aluminosilicates including synthetic zeolites typified by zeolites X, Y. ZSM-4, ZSM-5, ZSM-11, ZSM-21 etc. as well as naturally occurring zeolites such as erionite, faujasite, mordenite, etc.

The surface of the charge porous refractory metal oxide bears a plurality of pendant hydroxyl groups. Although it may be possible to use the porous refractory oxides as they are obtained, it is preferred to pretreat them preferably by heating to drive off water, at 50° C.–450° C. say 200° C. for 1–24 hours, say 6 hours at atmospheric pressure. In the case of silica, it may alternatively be desirable to pretreat by reaction in aqueous medium in liquid phase with a Bronsted acid, typically at 25° C.–100° C., say 100° C. for 1–24 hours, say 4 hours. Illustrative Bronsted acids include hydrogen halides, preferably hydrogen chloride.

During this pretreatment, it appears that additional groups including hydroxyl groups may be made available for reaction.

The pretreated refractory oxide is reacted with an organometallic alkoxide. These organometal compounds may have the formula $$(R'O)_{m-a-b}-\underset{\underset{R_b}{|}}{M}-R''_a$$

In the organometallic alkoxide, R' is a lower alkyl group having 1-8 carbon atoms including methyl, ethyl, propyls, butyls, hexyls, octyls, etc. Preferred R' groups may include methyl and more preferably ethyl.

R may be a lower alkyl group having 1-8 carbon atoms including methyl, ethyl, propyls, butyls, hexyls, actyls, etc. Preferred R groups may include methyl and more preferably ethyl.

R'' is a poly(oxyethylene) residue or a poly(oxypropylene) residue derived respectively from polyethylene glycol or polypropylene glycol. This residue may be characterized by the formula $$-O+CH_2-\underset{\underset{X}{|}}{CH}-O\!+\!_{\overline{n}}R^*$$

wherein X is hydrogen or methyl, preferably hydrogen. In the formula, n may be 1-300, preferably 8-42, say 20.

R* may be hydrogen or a lower C₁-C₈ alkyl hydrocarbon group, preferably methyl. It will be apparent to those skilled in the art that when R* is other than hydrogen, eg methyl, the residue may be derived from the mono ethers (eg the monomethyl ether) of polyethylene glycol or polypropylene glycol.

The organometal M, having a valence m greater than 1, in the formula, may be selected from the group consisting of silicon, phosphorus, aluminum, tin, titanium, and boron. (It will be appreciated by those skilled in the art that some of these such as silicon, boron, phosphorus, etc. may commonly be designated by designations other than metallic including metalloid, etc.; however they all form similar composition which may be used in the process of this invention and accordingly they are herein designated as organometal). Preferred of these organometals is silicon.

In the formula, the valence m, of the metal M, will be greater than 1. It may commonly be 2-5; and in the preferred embodiment it may be 4.

b may be 0 or an integer less than m−1. Commonly b may be 0-3 and in the preferred embodiment, b may be 0. When m is 5, b may be 0, 1, 2 or 3. When m is 4, b may be 0 or 1 or 2. When m is 3, b may be 0 or 1. When m is 2, b is 0.

The novel organometallic alkoxides which may be employed in practice of the process of this invention may typically include those listed in the following table, the first listed being preferred (in each case, n is typically 10, 20, or 40).

TABLE (EtO)₃ Si—O(̵CH₂CH₂O)ₙH
(EtO)₃ Si—O(̵CH₂CH₂O)ₙMe
(MeO)₃ Si—O(̵CH₂CH₂O)ₙMe
(EtO)₃ Si—O(̵CH₂CH₂O)ₙEt
(EtO)₃ Si—O(̵CH₂CH₂O)ₙPr (EtO)₂ Si—O(̵CH₂CH₂O)ₙH
  |
  CH₃

(MeO)₂ Si—[O(̵CH₂CH₂O)ₙH]₂

(EtO)₃ Si—O(̵CH₂CH O)ₙH
          |
          CH₃

TABLE-continued (EtO)₂ P—O(̵CH₂CH₂O)ₙH

PrO P ⎡—O(CH₂CH O)ₙH ⎤
      ⎢       |      ⎥
      ⎣       CH₃    ⎦₂

(PrO)₂P—O(̵CH₂CH O)ₙH
              |
              CH₃

(EtO)₄ P—O(̵CH₂CH₂O)ₙH
(EtO)₂ Al O(̵CH₂CH₂O)ₙH
(MeO) Al[—O(CH₂CH₂O)ₙMe]₂
(EtO)₃ Sn—O(̵CH₂CH₂O)ₙH (MeO)₃ Sn—O(̵CH₂CH O)ₙMe
                 |
                 CH₃

(MeO)₂ Sn—[O(̵CH₂CH₂O)ₙH]₂
(EtO)₃ Ti—O(CH₂CH₂O)ₙ̅H
MeO Sn[O(̵CH₂CH₂O)ₙH]₃

(MeO)₂ Sn—O(̵CH₂CH₂O)ₙH
       |
       Me

MeO B—O(̵CH₂CH₂O)ₙH
    |
    CH₃

In accordance with certain aspects of this invention the novel organometal alkoxides of polyalkylene glycols:

$$(R'O)_{m-a-b}-\underset{\underset{R_b}{|}}{M}-R''_a$$

may be prepared by the reaction of $$(R'O)_{m-b}\underset{\underset{R_b}{|}}{M} + a\ HR'' \longrightarrow (R'O)_{m-a-b}-\underset{\underset{R_b}{|}}{M}-R''_a + a\ R'OH$$

In a preferred embodiment wherein b is 0 and HR'' is $$HO+CH_2\underset{\underset{X}{|}}{CH}-O+Me,$$

the reaction may be $$(R'O)_m\ M + a\ HO+CH_2\underset{\underset{X}{|}}{CH}-O+Me \longrightarrow$$

$$(R'O)_{m-a}-M-O+CH_2\underset{\underset{X}{|}}{CH}+Me + a\ R'OH$$

Reaction is carried out preferably in liquid phase in inert solvent, typically an ether such as diethylether, or an aromatic hydrocarbon such as benzene, toluene, xylene, etc. Preferred solvent is toluene present in excess.

Reaction is carried out at temperature of 25° C.–200° C., say 110° C. (preferably at reflux temperature of the reaction mixture including solvent at preferably atmospheric pressure for 1-24 hours, say 1 hour during which the alcohol by-product (preferably ethanol) may be recovered in the overhead distillate.

In a typical preferred embodiment the following reaction may occur:

n = 10

Reaction is preferably carried out in this embodiment, in toluene reaction medium, by adding substantially equivalent (preferably equimolar) amounts of the organometallic composition eg tetra-ethoxy silicon (also properly nomenclated as tetraethyl orthosilicate) and monomethyl ether of polyethylene glycol. Commonly the organometallic composition may be present in slight deficiency or more preferably in slight excess. The mix is preferably heated at 25° C.-200° C., say 110° C. for 1-24 hours, say 1 hour. During reaction, by-product, typically ethanol may be distilled off or azeotropically removed. Product may be recovered by stripping off solvent at 25° C.-100° C., say 25° C. and 0.01-15 psig, say 0.1 psig. However commonly the product is not isolated; it is reacted (without isolating) with the metal oxide support.

In accordance with another embodiment of this invention, the compounds may be prepared by the reaction of

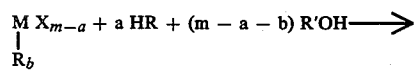

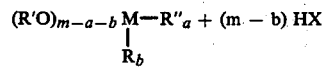

Reaction may be carried out preferably in inert solvent such as an ether, typified by diethyl ether, or an aromatic hydrocarbon such as toluene. The charge organometallic compound, preferably silicon tetrachloride, in solution in the inert solvent, preferably diethyl ether may be added to a reaction vessel. The compounds are preferably at minus 78° C.-plus 35° C. There may then be added substantially equivalent amounts of alcohol and of eg polyethylene glycol.

After addition, the reaction mixture may be heated to 25° C.-200° C., say 34° C. preferably to reflux temperature over 1-24 hours, say 2 hours. The solvent may then be stripped off at 25° C.-100° C., say 25° C. and 0.01-15 psig, say 0.1 psig.

The crude product so obtained is typically a viscous liquid white solid.

In a typical preferred reaction, the following may occur:

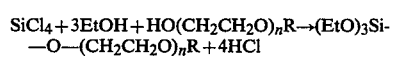

wherein n is 10.

The organometallic alkoxides containing a polyoxyalkylene residue may be used as catalysts, as surfactants, as stabilizers for polyvinylchloride resins (particularly the tin-containing compounds), etc. It is a feature of the process of this invention that the products of this invention, useful as phase transfer catalysts, may be formed by reaction of the (i) organometallic alkoxides containing a polyoxyalkylene residue with (ii) a porous refractory oxide.

During the reaction, the following may typically occur:

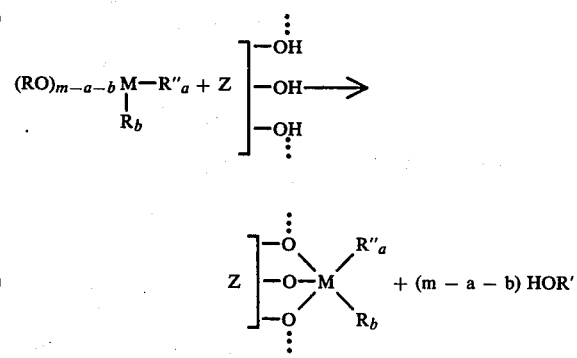

In the formulae, Z represents the porous refractory oxide body: and it may include oxide groups or hydroxide groups in addition to those which are shown. It should be noted that one oxygen-to-metal (—O—M) bond is sufficient to attached the organometallic alkoxides to the porous refractory oxide body; and if more than one O—M bond is formed, they need not be from adjacent OH groups. For simplicity, the reaction is shown with the above bonding.

It will be apparent that M will be bonded to the oxygen atom(s) of the preferably pretreated oxide by a number of bonds which reflects its valence and the number of R groups or of polyoxyalkylene moieties R'' which it bears originally. Clearly if M be trivalent as in the case of boron then the reaction may be of the form

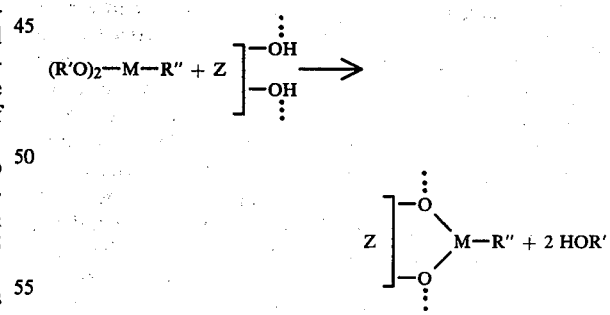

If M be tetravalent, as in the case of the preferred silicon, a typical reaction may for example be

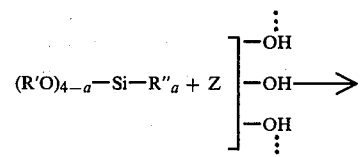

-continued

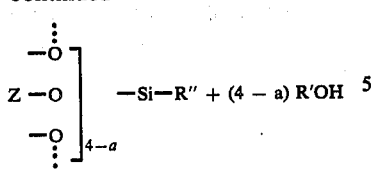

or specifically

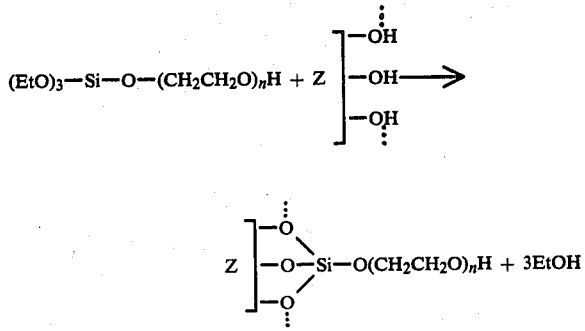

wherein n is 10.

Generally the product may be described as a porous refractory oxide bearing a plurality of groups

The glycol-containing groups

may be present typically in amount of 0.1–1, preferably 0.1–0.6, say about 0.3 millimoles of glycol per gram of support.

This reaction may be carried out in liquid phase by adding the refractory oxide (typically pretreated alumina or silica gel) to the crude reaction mixture containing the organometallic alkoxide of the polyoxyalkylene polyol. Preferably the ratio may be 0.0001–0.1 moles, typically 0.001–0.01 moles, say 0.002 moles of organometallic alkoxide per gram of refractory oxide. Reaction is preferably carried out in inert solvent which may be a hydrocarbon such as benzene, toluene, or xylene, or an ether such as ethyl ether. Preferably the same solvent is employed as is used in preparation of the alkoxide. The reaction mixture may be maintained at 25° C.–200° C., say 110° C. for 1–24 hours, say 3 hours.

After the reaction is complete, the product may be filtered and washed with fresh solvent. Air drying for 1–48 hours, say 24 hours at 25° C.–150° C., say 25° C. typically yields a white powder.

The products so prepared may be used as phase transfer catalysts. They are found to be particularly characterized by good yield and selectivity under moderate temperature and pressure conditions. They are also advantageous in that they may be prepared at moderate cost and they are easily recovered from the product mixture—usually by simple filtration.

It is a feature of this invention according to one of its aspects that the phase transfer catalysts of this invention may find particular use in reactions of the type

RA+EY→RY wherein R is a hydrocarbon group, bonded to A through a non-tertiary carbon atom, which may be an alkyl group, an aralkyl group, or a cycloalkyl group, including such radicals when inertly substituted. When R is alkyl, it may typically be methyl, ethyl, n-propyl, iso-propyl, n-butyl, 1-butyl, sec-butyl, amyl, octyl, decyl, octadecyl, etc. When R is aralkyl, it may typically be benzyl, beta-phenylethyl, etc. When R is cycloalkyl, it may typically be cyclohexyl, cycloheptyl, cyclooctyl, 2-methylcycloheptyl, 3-butylcyclohexyl, 3-methylcyclohexyl, etc. R may be inertly substituted i.e. it may bear a non-reactive substituent such as alkyl, aryl, cycloalkyl, ether, nitro, etc. Typically inertly substituted R groups may include, 2-ethoxyethyl, carboethoxymethyl, 4-methyl cyclohexyl, etc. The preferred R groups may be lower alkyl, i.e. $C_1$–$C_{10}$ alkyl, group including eg methyl ethyl, n-propyl, i-propyl, butyls, amyls, hexyls, octyls, decyls, etc. R may preferably be n-butyl.

A in the above formula is a halide, preferably an active halide i.e. bromide or iodide.

Typical R** A compositions may include 1-bromobutane, 1-iodobutane, 2-bromobutane, benzyl bromide, benzyl chloride, 3-chloro-1-pentene, cyclohexyl bromide, etc. Preferred may be alkyl halides such as 1-bromobutane.

The compound EY is a nucleophile typified by those wherein E is a cation (including reaction medium-soluble cations), preferably an alkali metal or alkaline earth metal. Preferred is sodium. Y may be any reaction medium-soluble anion (eg a carboxylate) of an organic acid typified by formate, acetate, succinate, etc. Preferred EY may be sodium acetate or potassium acetate.

The reaction, typically between 1-bromobutane and potassium acetate to yield butyl acetate may be carried out at 15° C.–150° C., preferably at ambient temperature of about 20° C. for 1–24 hours, say about 12 hours—depending upon the yield desired. Reaction is preferably carried out in solvent. If it found that use of water or hydrocarbons such as toluene as solvent is satisfactory; but presence of both solvents is unsatisfactory.

The ability of the novel catalyst system of this invention to function as a phase transfer catalyst may be illustrated by the reaction wherein 1-bromobutane is converted to normal butyl acetate by reaction in water solvent or in toluene solvent, with a nucleophile typified by a salt of acetic acid such as potassium acetate. No reaction is observed between 1-bromobutane and potassium acetate (in either toluene or water) in absence of any catalyst—0% conversion to n-butyl acetate is observed. Similar results are achieved when the "catalyst" is unfunctionalized silica or unfunctionalized alumina at toluene reflux temperature. However, use of the preferred catalyst of this invention permits attainment of 22%–66% conversion after 3 hours and up to 97% conversion after 24 hours. Reaction in either toluene or water solvent result in comparable conversions. Other nucleophiles also prove effective under these reaction conditions using the preferred catalyst system. Normal butyl iodide was obtained in 97% conversion after only 1 hour reaction time using 1-bromobutane and sodium iodide as the reactants.

In accordance with certain of its aspects, this invention is directed to a process for oxidizing a hypochlorite-oxidizable group which comprises maintaining a compound bearing a hypochlorite oxidizable hydroxyl group or amino group or amide group or aldehyde group at oxidizing conditions in the presence of, as catalyst a porous refractory oxide composition bearing a plurality of groups

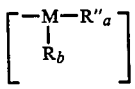

wherein

M is an atom having a valence m greater than 1 selected from the group consisting of silicon, phosphorus, aluminum, titanium, tin, and boron;

R is a lower alkyl hydrocarbon group having 1–8 carbon atoms;

R'' is a poly(oxyethylene) or poly(oxypropylene) residue having the formula

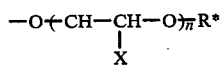

X is hydrogen or methyl;
a is a positive integer less than m;
b is 0 or a positive integer less than m−2; and
n is 1–300; and
R* is hydrogen or a lower alkyl hydrocarbon group containing 1–8 carbon atoms.

Hypochlorite-oxidizable groups include:
(i) hydroxy groups bonded to a primary or secondary carbon atom—which may be oxidized to an aldehyde, ketone, or to an acid;
(ii) amine groups bonded to a primary carbon atom—which may be oxidized to a nitrile;
(iii) amide groups—which may be oxidized to a nitrile;
(iv) aldehyde groups—which may be oxidized to an acid; etc.

Compounds which may be oxidized include those wherein the oxidizable hydroxy or amine groups are bonded to a primary or secondary carbon in a hydrocarbon chain derived from an alkane, an alkene, an alkyne, a cycloalkane, a cycloalkene, or an arylalkane. When the group is an —OH group, the preferred compounds which may be oxidized include monoalcohols such as ethanol, propanol, butanols, 2-ethylhexanol, benzyl alcohol, etc. When the group is an —NH₂ group, the preferred compounds which may be oxidized include primary mono-amines such as ethyl amine, propyl amine, butyl amine, cyclohexyl amine, benzyl amine, etc. See U.S. Pat. No. 3,996,259 and Dehnlow et al *Phase Transfer Catalysts* Verlag Chemie, Weinheim (1980).

The oxidized product in the case of the amine is the nitrile. Thus ethyl amine may be oxidized to acetonitrile; benzyl amine may be oxidized to benzonitrile, etc.

When the oxidizable group is a hydroxy group the oxidation product may be the aldehyde, ketone, or the acid. Thus ethanol may be oxidized to acetic acid; propanol may be oxidized to propanal or propanoic acid; etc.

In the case of an amide group, a typical reaction may be the oxidation of acetamide to acetonitrile.

In the case of an aldehyde group, a typical reaction may be the oxidation of acetaldehyde to acetic acid. In the case of a compound containing an activated double bond, a typical reaction may be the oxidation of propene to propylene glycol.

It is however a particular feature of this invention that the novel catalyst system permits selective oxidation of benzyl alcohol to benzaldehyde with little or no coproduction of the corresponding acid. Oxidation with hypohalite is typically carried out at 15° C.–150° C., say 20° C. Although temperatures at or below reflux temperature may be employed, it is preferred to use ambient temperature over 1–24 hours, say 24 hours. Reaction is preferably carried out in 4 w %–6 w % aqueous sodium hypochlorite solution in the presence of organic co-solvent. Preferred organic co-solvents may include halogenated hydrocarbons such as methylene chloride (CH₂Cl₂), esters such as ethyl acetate, etc. Mixtures of co-solvents may be employed.

The selective oxidation of benzyl alcohol is typically carried out using an aqueous sodium hypochlorite solution (4–6%) and an organic co-solvent. Organic co-solvent may include esters of carboxylic acids typified by alkyl acetates such as ethyl acetate; or halogenated hydrocarbons such as methylene chloride CH₂Cl₂. The mixture is stirred at room temperature for 24 hours. In the absence of any catalyst only a 6% conversion to benzaldehyde is observed using methylene chloride as the co-solvent. When the "catalyst" is unfunctionalized alumina a 20% conversion is noted after 24 hours. When the preferred catalyst is used, in particular the alkyl ether derivatives immobilized on alumina, a 51% conversion is observed with methylene chloride as the organic co-solvent and a 69% conversion is obtained using ethyl acetate as co-solvent. The alkyl ethers are the preferred catalysts as the glycols themselves may contain oxidizable alcohol functionality.

It is a particular feature of the catalysts produced by the process of this invention that they may possess specificity. For example catalyst using an alumina substrate may be found to be more desirable when used in aqueous medium. Catalysts using a silica substrate may be found to be preferred when the reaction is carried out in non-aqueous media. For mixed media, such as toluene-water, the preferred substrate may be alumina.

DESCRIPTION OF PREFERRED EMBODIMENTS

Practice of the novel process of this invention may be apparent from the following description of preferred embodiments.

All reactions were carried out using reagent grade materials with no prior purification. Silica gel (W. R. Grace, grade 62, 60–200 mesh) was pretreated by refluxing in concentrated hydrochloric acid (37%) for four hours followed by repeated washings with water then acetone and drying under vacuum at 80° C. The alumina (Aldrich, neutral, chromatographic grade) was pretreated by heating at 200° C. for 6 hours under vacuum. All experiments were routinely done under an inert atmosphere.

CATALYST PREPARATION

Example I

Reaction of Tetraethyl Orthosilicate, Polyethylene Glycol (average m.w. 400) and Silica Gel.

In this example which represents practice of a preferred embodiment, there was added to a 250 ml 3-neck flask, fitted with a mechanical stirrer and DeanStark trap with reflux condenser, 10 g (48 mmoles) tetraethyl orthosilicate, 15 g (37 mmoles) polyethylene glycol (mw 400) and 200 ml toluene. The mixture was heated at reflux 1 hour; and 50 ml distillate was removed.

Silica gel (40 g) was added and the mixture heated at reflux 2 hours at which time an additional 50 ml distillate was removed through the trap. The pot was cooled, an additional 50 ml toluene was added and the mixture was again heated at reflux for 1 hour with the subsequent removal of an additional 50 ml distillate. After cooling, the product was filtered, washed with 50 ml fresh toluene and 50 ml diethyl ether and air dried overnight to afford 49 g of a white powder which had a percent carbon composition of 8.8 (% C).

Example II
Reaction of Tetraethyl Orthosilicate, Polyethylene Glycol (average mw 1000), and Silica Gel.

Into a flask described in Example I was added 10 g (48 mmoles) tetraethyl orthosilicate, 25 g (25 mmoles) polyethylene glycol (mw 1000) and 200 ml toluene. The reaction procedure and work-up followed the same as Example I with 40 g silica gel except 25 ml distillate was removed after each reflux period. Air drying of the solid produced 52 g of a white powder containing 11.1% C.

Example III
Reaction of Tetraethyl Orthosilicate, Polyethylene Glycol (average m.w. 1500), and Silica Gel.

Into a flask equipped as in Example I was added 10 g (48 mmoles) tetraethyl orthosilicate, 30 g (20 mmoles) polyethylene glycol (m.w. 1500) and 200 ml toluene. The same reaction conditions and work-up as Example I were followed with 40 g silica gel. Air drying afforded a white powder (52 g) containing 11.8% C.

Example IV
Reaction of Tetraethyl Orthosilicate, Polyethylene Glycol (average m.w. 400), and Alumina.

The same procedure and amount of reactants as in Example I was followed except 40 g of alumina was used in place of silica gel and only 25 ml distillate was removed after each reflux. Drying overnight yielded a white powder (47 g) containing 4.7% C.

Example V
Reaction of Tetraethyl Orthosilicate, Polyethylene Glycol (average m.w. 1500), and Alumina.

The same procedure as in Example I was followed (same reactants) except 40 g alumina was substituted for the silica gel and only 25 ml distillate was removed each time. Drying overnight afforded a white powder (60 g) containing 16% C.

Example VI
Reaction of Tetraethyl Orthosilicate, Polyethylene Glycol Monomethyl Ether (average m.w. 350), and Silica Gel.

Into a flask fitted as in Example I was added 10 g (48 mmoles) tetraethyl orthosilicate, 15 g (43 mmoles) polyethylene glycol monomethyl ether (mw 350), and 200 ml toluene. Reaction conditions and work-up followed those in Example I with 40 g silica gel except only 25 ml distillate was removed after each reflux period. The white powder was dried by stripping residual solvent on a rotary evaporator at room temperature under water aspirator vacuum to yield 49 g containing 7.5% C.

Example VII
Reaction of Tetraethyl Orthosilicate, Polyethylene Glycol Monomethyl Ether (average m.w. 750), and Silica Gel.

The same procedure as in Example VI was followed using instead 20 g (27 mmoles) polyethylene glycol monomethyl ether (m.w. 750). Drying of the solid yielded a white powder (52 g) containing 10.5% C.

Example VIII
Reaction of Tetraethyl Orthosilicate, Polyethylene Glycol Monomethyl Ether (average m.w. 1900), and Silica Gel.

The same procedure as in Example VI was followed using instead 30 g (16 mmoles) polyethylene glycol monomethyl ether (m.w. 1900). Drying of the solid yielded a white powder (54 g) containing 12.2% C.

Example IX
Reaction of Silicon Tetrachloride, Ethanol, Polyethylene Glycol (average m.w. 400), and Silica Gel.

Into a 250 ml 3-neck flask fitted with a magnetic stirrer, reflux condenser and dropping funnel was added 8 g (47 mmoles) silicon tetrachloride and 100 ml anhydrous diethyl ether. The mixture was cooled in an ice bath and 7 g (152 mmoles) ethanol and 20 g (50 mmoles) polyethylene glycol (m.w. 400) were added slowly over 1 hour. The ice bath was removed after complete addition and the mixture refluxed for 2 hours. The solvent was stripped at room temperature under water aspirator vacuum to afford 27 g of a clear colorless liquid. The crude product (25 g, 45 mmoles) was added to a 250 ml 3-neck flask equipped with a mechanical stirrer and Dean-Stark trap with a reflux condenser.

Toluene (175 ml) and 40 g silica gel were added and the mixture heated at reflux for 2 hours. Distillate (25 ml) was removed, 25 ml fresh toluene added and the mixture refluxed an additional 1 hour at which point another 25 ml distillate was taken off. Upon cooling, the product was filtered, washed with 50 ml fresh toluene and then with 50 ml diethyl ether. Drying the solid at room temperature and water aspirator vacuum afforded a white powder (48 g) which contained 7.8% C.

Example X
Reaction of Silicon Tetrachloride, Ethanol, Polyethylene Glycol (average m.w. 1500), and Silica Gel.

The same procedure as in Example IX was followed using instead 30 g (20 mmoles) polyethylene glycol (m.w. 1500). The crude tetraalkoxy derivative (42 g) and 40 g silica gel were reacted as in Example IX yielding a white powder (57 g) containing 13.5% C.

Example XI
Reaction of Silica Tetrachloride, Ethanol, Polyethylene Glycol Monomethyl Ether (average m.w. 350), and Silica Gel.

The same procedure as in Example IX was followed using instead 20 g (57 mmoles) polyethylene glycol monomethyl ether (m.w. 350). The crude tetralkoxy derivative (25 g) and 40 g silica gel were reacted as in Example IX yielding a white powder (52 g) containing 9.7% C.

Example XII

Reaction of Silicon Tetrachloride, Ethanol, Polyethylene Glycol Monomethyl Ether (average m.w. 1900), and Silica Gel.

The same procedure as in Example IX was followed using instead 30 g (16 mmoles) polyethylene glycol monomethyl ether (m.w. 1900). The crude tetraalkoxy derivative (37 g) and 40 g silica gel were reacted as in Example IX to afford a white powder (86 g) containing 14.4% C.

Example XIII

Reaction of Silicon Tetrachloride, Ethanol, Polyethylene Glycol Monomethyl Ether (average m.w. 350) and Alumina.

Into a 1 liter preweighed 3-neck flask fitted with a magnetic stirrer, reflux condenser and addition funnel was added 20 g (0.12 moles) silicon tetrachloride and 250 ml. anhydrous ether. The mixture was cooled in an ice bath and 17.5 g (0.38 mmoles) ethanol and 50 g (0.14 moles) polyethylene glycol monomethyl ether (m.w. 350) were added slowly over 1 hour. The ice bath was removed after complete addition and the mixture heated at room temperature under water aspirator vacuum to afford 69 g of a clear colorless liquid.

The crude product (69 g, 0.12 moles) was added to a 1 liter 3-neck flask equipped with a mechanical stirrer and Dean-Stark trap with a reflux condenser. Toluene (500 ml) and 200 g alumina were added and the mixture heated at reflux for 2 hours. Distillate (50 ml) was removed, the mixture heated an additional 1 hour at reflux at which point another 50 ml distillate was taken off. Upon cooling, the product was filtered and the solid washed slowly with 100 ml fresh toluene and then with 100 ml diethyl ether. Drying the solid at 50° C. and water aspirator vacuum afforded a white powder (239 g) which contained 7.6% C.

In summary, the catalysts so prepared may be as follows:

TABLE

| CATALYST PREPARATION | | |
|---|---|---|
| Example | % C | MMoles glycol/gram Support (approx.) |
| I | 8.8 | 0.42 |
| II | 11.1 | 0.21 |
| III | 11.8 | 0.15 |
| IV | 4.7 | 0.22 |
| V | 16 | 0.20 |
| VI | 7.5 | 0.41 |
| VII | 10.5 | 0.26 |
| VIII | 12.2 | 0.12 |
| IX | 7.8 | 0.37 |
| X | 13.5 | 0.17 |
| XI | 9.7 | 0.52 |
| XII | 14.4 | 0.14 |
| XIII | 7.6 | 0.42 |

CATALYST EVALUATION

Example XIV

Reaction of product of Example XI with 1-Bromobutane and Potassium Acetate in Toluene Solvent.

Into a 250 ml 3-neck flask fitted with a magnetic stirrer and reflux condenser was added 25 g (0.25 moles) potassium acetate, 70 ml toluene, and 7 g n-decane as an internal standard. To this mixture was added 20 g (0.0104 moles) of the catalyst of Example XI and 7 g (0.05 moles) 1-bromobutane. The solution was heated to reflux for 3 hours and after cooling filtered through a medium sintered glass funnel. The filter cake was washed slowly with 50 ml methylene chloride.

The filtrate was transferred to a simple distillation apparatus and the solvent distilled off to a head temperature of 75° C. Analysis of the residue by gas chromatography showed a 66% conversion to n-butyl acetate (57% yield).

Example XV

Reaction of product of Example IV with 1-Bromobutane and Potassium Acetate in Water Solvent.

Into a 100 ml 3-neck flask fitted with a mechanical stirrer and reflux condenser was added 50 ml water, 18 g (0.18 moles) potassium acetate, 5 g (0.036 moles) 1-bromobutane and 20 g (0.0044 moles) catalyst of Example IV.

After heating to reflux for 3 hours, the mixture was filtered, the solid washed with 65 ml methylene chloride and the combined filtrate transferred to a separatory funnel. The organic layer was withdrawn and saved. The aqueous phase was washed twice with 25 ml methylene chloride and the combined organic washings dried over anhydrous sodium sulfate. Gas chromatographic analysis of the product indicated a 49% conversion to n-butyl acetate.

The following Table tabulates the % Conversion of 1-bromobutane to butyl acetate obtained in Examples XIV–XV as well as in other Examples which followed the procedure of Examples XIV–XV except that the catalyst used was that prepared in the Example set forth in column 2, which also shows the number of millimoles employed. The results set forth in the Table are those obtained with a mole ratio (potassium acetate to 1-bromobutane) of 5:1. However the reaction does proceed in good yield when only a stoichiometric amount of potassium acetate is used. In each case, the solvent employed was toluene, except in Examples XIX and XXI wherein it was water. The reaction time (hours) and the temperature (°C.) are set forth as is the % Conversion of 1-bromobutane to butyl acetate. It will be noted that in the Table, the listing for Example XX is a summary of the data from Example XV supra and that for Example XXVIII is a summary of the data from Example XIV supra.

It will be particularly noted that if the reaction of Example XVI (carried out over 3 hours to give a conversion of 61%) be extended to 24 hours, as in Example XXX, the conversion is increased to 97%.

TABLE

| CATALYST EVALUATION Preparation of Butyl Acetate from 1-Bromobutane and Potassium Acetate | | | |
|---|---|---|---|
| | Catalyst | Reaction Conditions | |
| Example | (mmole) | Time hrs/Temp. °C. | % Conversion |
| XVI | I (8.4) | 3/110 | 61% |
| XVII | II (4.2) | 3/110 | 39% |
| XVIII | III (3) | 3/110 | 43% |
| XIX | IV (4.4) | 3/110 | 29% |
| XX | IV (4.4) | 3/100 | 49% |
| XXI | V (4) | 3/110 | 37% |
| XXII | V (4) | 3/100 | 52% |
| XXIII | VI | 3/110 | 39% |

TABLE-continued
CATALYST EVALUATION
Preparation of Butyl Acetate from 1-Bromobutane and Potassium Acetate

| Example | Catalyst (mmole) | Reaction Conditions Time hrs/Temp. °C. | % Conversion |
|---|---|---|---|
| XXIV | VII (8.2) | 3/110 | 22% |
| XXV | VIII (5.2) | 3/110 | 48% |
| XXVI | IX (2.4) | 3/110 | 47% |
| XXVII | X (7.4) | 3/110 | 44% |
| XXVIII | XI (3.4) | 3/110 | 66% |
| XXIX | XII (10.4) | 3/110 | 38% |
| XXX | I (2.8) | 24/110 | 97% |
| | (8.4) | | |

CATALYST EVALUATION

Example XXXI

Reaction of product of Example IV with 1-bromobutane and sodium acetate in water solvent.

Into a 100 ml 3-neck flask fitted with a mechanical stirrer and reflux condenser was added 70 ml water, 21 g (0.26 moles) sodium acetate, 7 g (0.051 moles) 1-bromobutane, 20 g (0.0044 moles) catalyst of Example IV and 7 g n-decane as an internal standard.

After heating to reflux for 3 hours, 50 ml methylene chloride was added and the mixture was filtered. The solid was washed slowly with 50 ml fresh methylene chloride and the filtrate transferred to a separatory funnel. The organic layer was withdrawn and saved. The aqueous phase was washed twice with 25 ml methylene chloride and the combined organic washings dried over anhydrous sodium sulfate. Gas chromatographic analysis of the product inicated a 55% conversion to n-butyl acetate (26% yield).

TABLE
CATALYST EVALUATION
Preparation of Butyl Acetate from 1-Bromobutane and Sodium Acetate

| Example | Catalyst (mmole) | Reaction Conditions Time hrs/Temp. °C. | % Conversion |
|---|---|---|---|
| XXXI | IV (4.4) | 3/110 | 55% |

Example XXXII

Reaction of product of Example I with 1-Bromobutane and sodium iodide in toluene solvent.

Into a 250 ml 3-neck flask fitted with a magnetic stirrer and reflux condenser was added 70 ml toluene, 38 g (0.85 moles) sodium iodide, 7 g (0.051 moles) 1-Bromobutane, 20 g (0.0084 moles) catalyst of Example I and 7 g n-decane as an internal standard. The solution was heated to reflux for 3 hours and after cooling filtered through a sintered glass funnel. The filter cake was washed slowly with 50 ml methylene chloride.

The filtrate was transferred to a simple distillation apparatus and the solvent distilled off to a head temperature of 75° C. Analysis of the residue by gas chromatography showed a 100% conversion to n-butyl iodide (80% yield).

Example XXXIII

In this example, the procedure of Example XXXII was followed except that the time of reaction (reflux) was one hour instead of three hours.

TABLE
CATALYST EVALUATION
Preparation of 1-Iodobutane from 1-Bromobutane and Sodium Iodide

| Example | Catalyst (mmole) | Reaction Conditions Time hrs/Temp. °C. | % Conversion |
|---|---|---|---|
| XXXII | I (8.4) | 3/110 | 100% |
| XXXIII | I (8.4) | 1/110 | 94% |

Example XXXIV

Oxidation of benzyl alcohol with hypochlorite using the product of Example XIII.

Into a 250 ml 3-neck flask fitted with a mechanical stirrer and reflux condenser is added 4 g (0.02 moles) benzyl alcohol, 75 ml ethyl acetate and 20 g (0.0084 moles) catalyst of Example XIII. The mixture is stirred 15 minutes and 75 ml (0.05 moles) of a 4-6% aqueous sodium hypochlorite solution is slowly added over 20 minutes while maintaining the pot temperature at 20° C. with an ice bath. The mixture is stirred 24 hours at room temperature.

The crude mixture is filtered and the filter cake washed with 50 ml methylene chloride. The filtrate is transferred to a separatory funnel and the organic layer withdrawn and saved. The aqueous layer is washed twice with 25 ml methylene chloride, the organic layer is combined and the solvent distilled off. Gas chromatographic analysis of the product indicated at 69% conversion to benzaldehyde.

The following table tabulates the % conversion of benzyl alcohol to benzaldehyde obtained in Example XXXIV as well as in other Examples which followed the procedure of Example XXXIV except that the catalyst used was that set forth in column 2 and the organic co-solvent was that set forth in column 3. The reaction time (hours) and the temperature are set forth as is the % conversion of benzylalcohol to benzaldehyde. It will be noted that in the Table, the listing for Example XXXIX is a summary of the data from Example XXXIV supra. It should be noted that the reaction in the absence of catalyst, as in Example XXXV does result in a 6% conversion and that when unfunctionalized alumina (20 g) is used as a "catalyst", as in Example XXXVI, a 21% conversion results. Also, for conversion to benzaldehyde, ethyl acetate appears to be the organic co-solvent of choice.

TABLE
CATALYST EVALUATION
Preparation of Benzaldehyde from Benzyl Alcohol and Sodium Hypochlorite

| Example | Catalyst (mmole) | Organic Co-solvent | Reaction Conditions Time hrs/Temp. °C. | % Conversion |
|---|---|---|---|---|
| XXXV | none | methylene chloride | 24/25 | 6% |

TABLE-continued
CATALYST EVALUATION
Preparation of Benzaldehyde from Benzyl Alcohol and Sodium Hypochlorite

| Example | Catalyst (mmole) | Organic Co-solvent | Reaction Conditions Time hrs/Temp. °C. | % Conversion |
|---|---|---|---|---|
| XXXVI | unfunctionalized alumina | methylene chloride | 24/25 | 21% |
| XXXVII | XIII (8.4) | methylene chloride | 24/25 | 51% |
| XXXVIII | XIII (8.4) | methylene chloride* ethyl acetate | 24/25 | 48% |
| XXXIX | XIII (8.4) | ethyl acetate | 24/25 | 69% |

*a mixture of equal parts by weight

Results comparable to the above may be obtained if the novel organometallic alkoxide (which has been attached to a metal oxide substrate), prepared in manner comparable to the previous examples, is:

| Example | Organomettalic Alkoxide |
|---|---|
| XXXX | 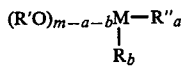 |
| XXXXI | 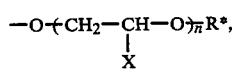 |

Although this invention has been illustrated by reference to specific embodiments, it will be apparent to those skilled in the art that various changes and modifications may be made which clearly fall within the scope of this invention.

I claim:

1. The process for preparing a solid functionalized porous refractory oxide which comprises (i) reacting a porous refractory oxide, bearing surface hydroxyl groups, with 0.0001-0.1 moles per gram of oxide of an organometal compound $$(R'O)_{m-a-b}M-R''_a$$
$$\qquad\qquad|$$
$$\qquad\qquad R_b$$

wherein R' is a lower alkyl hydrocarbon group having 1-8 carbon atoms, R is a lower alkyl hydrocarbon group having 1-8 carbon atoms, R'' is a poly(oxyethylene) or poly(oxypropylene) residue having the formula $$-O(CH_2-CH-O)_{\overline{n}}R^*,$$
$$\qquad\quad|$$
$$\qquad\quad X$$

R* is hydrogen or a lower alkyl hydrocarbon group containing 1-8 carbon atoms, X is hydrogen or methyl, n is 1-300, M is an atom having a valence m greater than 1 selected from the group consisting of silicon, phosphorus, aluminum, tin, titanium, and boron, a is a positive integer less than m, and b is 0 or an integer less than m−1, thereby splitting out alcohol R'OH and forming solid functionalized oxide bearing at least one —O—M—R'' group on the surface of said oxide; and (ii) recovering said solid functionalized oxide bearing at least one —O—M—R'' group on the surface thereof.

2. The process for preparing a functionalized porous refractory oxide as claimed in claim 1 wherein said oxide is silica.

3. The process for preparing a functionalized porous refractory oxide as claimed in claim 1 wherein said oxide is a silica gel which has been pretreated by contact with a Bronsted acid.

4. The process for preparing a functionalized porous refractory oxide as claimed in claim 1 wherein said oxide is alumina.

5. The process for preparing a functionalized porous refractory oxide as claimed in claim 1 wherein said oxide is alumina which has been pretreated by heating at 50° C.-450° C. for 1-24 hours.

6. The process for preparing a functionalized porous refractory oxide as claimed in claim 1 wherein said organometal compound is an organosilicon compound wherein M is silicon.

7. The process for preparing a functionalized porous refractory oxide as claimed in claim 1 wherein said organometal compound is

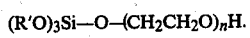

8. The process for preparing a functionalized porous refractory oxide as claimed in claim 1 wherein said organometal compound is

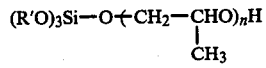

9. The process for preparing a functionalized porous refractory oxide as claimed in claim 1 wherein said organometal compound is

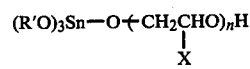

10. The process for preparing a functionalized porous refractory oxide as claimed in claim 1 wherein said organometal compound is

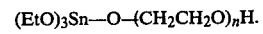

11. The process for preparing a functionalized porous refractory oxide as claimed in claim 1 wherein said organometal compound is

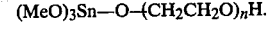

12. The process for preparing a solid functionalized porous refractory oxide which comprises (i) reacting in aqueous medium a Bronsted acid and a solid porous refractory oxide thereby forming a pretreated solid porous refractory oxide bearing hydroxyl groups;

(ii) reacting said pretreated solid porous refractory oxide, bearing hydroxyl groups, with 0.0001–0.1 moles per gram of oxide of an organometal compound

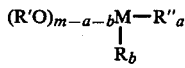

wherein R' is a lower alkyl hydrocarbon group having 1–8 carbon atoms, R is a lower alkyl hydrocarbon group having 1–8 carbon atoms, R'' is a poly(oxyethylene) or poly(oxypropylene) residue having the formula

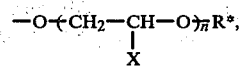

R* is hydrogen or a lower alkyl hydrocarbon group containing 1–8 carbon atoms, X is hydrogen or methyl, n is 1–300, M is an atom having a valence m greater than 1 selected from the group consisting of silicon, phosphorus, aluminum, tin, titanium, and boron, a is a positive integer less than m, and b is 0 or an integer less than m−1, thereby splitting out alcohol R'OH and forming solid functionalized oxide bearing at least one —O—M—R'' group on the surface of said oxide; and (iii) recovering said solid functionalized oxide bearing at least one —O—M—R'' group on the surface thereof.

13. The process for preparing a solid functionalized silica which comprises (i) reacting in aqueous medium a Bronsted acid and silica gel thereby forming a pretreated silica bearing hydroxyl groups;

(ii) reacting said silica with 0.0001–0.1 moles per gram of silica (EtO)$_3$Si—O—(CH$_2$CH$_2$O)$_n$Me wherein n is 1–300 thereby forming a functionalized silica wherein at least one Si—O—(CH$_2$CH$_2$O)$_n$Me group is bonded to the surface of the silica through at least one O—Si linkage; and (iii) recovering said functionalized silica bearing at least one Si—O—CH$_2$CH$_2$O—$_n$Me.

14. A solid porous refractory oxide composition bearing 0.0001–0.1 moles per gram of oxide of groups

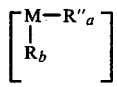

wherein

M is an atom having a valence m greater than 1 selected from the group consisting of silicon, phosphorus, aluminum, tin, titanium, and boron;

R is a lower alkyl hydrocarbon group having 1–8 carbon atoms;

R'' is a poly(oxyethylene) or poly(oxypropylene) residue having the formula

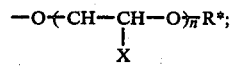

X is hydrogen or methyl;

a is a positive integer less than m;

b is 0 or a positive integer less than m−2; and n is 1–300; and

R* is hydrogen or a lower alkyl hydrocarbon group containing 1–8 carbon atoms.

15. A composition as claimed in claim 14 wherein the porous refractory oxide is silica gel.

16. A composition as claimed in claim 14 wherein the porous refractory oxide is alumina.

17. A composition as claimed in claim 14 wherein M is silicon.

18. A composition as claimed in claim 14 wherein M is tin.

19. A composition as claimed in claim 14 wherein M is aluminum.

20. A porous refractory oxide containing silica or alumina, bearing 0.0001–0.1 moles per gram of oxide of groups

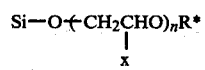

wherein X is hydrogen or methyl, n is 1–300, and R* is hydrogen or methyl.

21. The process for preparing a solid functionalized porous refractory oxide which comprises (i) reacting a porous refractory oxide bearing surface hydroxyl groups with 0.0001–0.1 moles per gram of oxide of

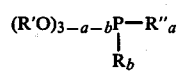

wherein R and R' are lower C$_1$–C$_8$ alkyl hydrocarbon groups, R'' is a poly(oxyethylene) or poly(oxypropylene) residue having the formula

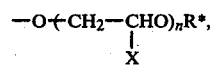

R* is hydrogen or lower C$_1$–C$_8$ alkyl hydrocarbon, X is hydrogen or methyl, n is 1–300, a is a 1 or 2, b is 0, 1, or 2, thereby splitting out alcohol R'OH and forming functionalized oxide bearing at least one —O—P—R'' on the surface of said solid oxide, and (ii) recovering said functionalized solid oxide bearing at least one —O—P—R'' group on the surface thereof.

22. The process for preparing a solid functionalized silica or alumina which comprises (i) reacting a porous refractory silica gel bearing hydroxyl groups with 0.0001–0.1 moles per gram of oxide of (EtO)$_2$P—O(CH$_2$CH$_2$O)$_n$H wherein n is 1–300 thereby forming solid functionalized silica gel bearing at least one —O—P—O—(CH$_2$CH$_2$O)$_n$H group on the surface of said silica; and (ii) recovering said solid functionalized silica gel bearing at least one —O—P—O(CH$_2$CH$_2$O)H group on the surface thereof.

23. The process for preparing a solid functionalized porous refractory oxide which comprises
(i) reacting a porous refractory oxide bearing surface hydroxyl groups with 0.0001–0.1 moles per gram of oxide of

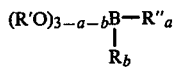

wherein R and R' are lower $C_1$–$C_8$ alkyl hydrocarbon groups, R" is a poly(oxyethylene) or poly(oxypropylene) residue having the formula

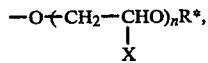

R* is hydrogen or lower $C_1$–$C_8$ alkyl hydrocarbon, X is hydrogen or methyl, n is 1–300, a is a 1 or 2, b is 0, 1, or 2, thereby splitting out alcohol R'OH and forming functionalized oxide bearing at least one —O—B—R" on the surface of said solid oxide, and
(ii) recovering said functionalized solid oxide bearing at least one —O—B—R" group on the surface thereof.

24. The process for preparing a solid functionalized silica or alumina which comprises
(i) reacting a porous refractory silica gel bearing hydroxyl groups with 0.0001–0.1 moles per gram of oxide of $(EtO)_2B$—O—$(CH_2CH_2O)_n$H wherein n is 1–300 thereby forming solid functionalized silica gel bearing at least one O—B—O—$(CH_2CH_2O)_n$H group on the surface of said silica; and
(ii) recovery said solid functionalized silica gel bearing at least one —O—B—O$(CH_2CH_2O)_n$H group on the surface thereof.

* * * * *

UNITED STATES PATENT AND TRADEMARK OFFICE
CERTIFICATE OF CORRECTION

PATENT NO. : 4,474,704
DATED : October 2, 1984
INVENTOR(S) : ROBERT A. SAWICKI

It is certified that error appears in the above—identified patent and that said Letters Patent is hereby corrected as shown below:

Column 5, line 56, after "liquid", insert --or--;

Column 6, line 29, correct the spelling of "attach";

Column 8, line 45, cancel "If it", insert --It--;

Column 17, line 21, correct the spelling of "organometallic";

Column 22, line 8, cancel "or alumina".

Signed and Sealed this

Second Day of April 1985

[SEAL]

Attest:

DONALD J. QUIGG

Attesting Officer     Acting Commissioner of Patents and Trademarks